(12) United States Patent
Annunziata

(10) Patent No.: US 10,238,518 B2
(45) Date of Patent: Mar. 26, 2019

(54) IMPLANTABLE WEIGHT CONTROL DEVICE

(75) Inventor: Gary Annunziata, Rancho Mirage, CA (US)

(73) Assignee: AGT INC., Rancho Mirage, CA (US)

( * ) Notice: Subject to any disclaimer, the term of this patent is extended or adjusted under 35 U.S.C. 154(b) by 1328 days.

(21) Appl. No.: 11/711,364

(22) Filed: Feb. 27, 2007

(65) Prior Publication Data

US 2008/0208135 A1    Aug. 28, 2008

(51) Int. Cl.
*A61F 5/00*    (2006.01)

(52) U.S. Cl.
CPC ............ *A61F 5/0079* (2013.01); *A61F 5/003* (2013.01)

(58) Field of Classification Search
CPC .................. A61F 5/0003; A61F 5/0013; A61F 5/003–5/0046
USPC ................. 606/191, 192; 604/103.06–103.09
See application file for complete search history.

(56) References Cited

U.S. PATENT DOCUMENTS

| | | | | |
|---|---|---|---|---|
| 4,485,805 A | * | 12/1984 | Foster, Jr. .................... | 128/898 |
| 4,796,629 A | * | 1/1989 | Grayzel ........................ | 606/194 |
| 4,899,747 A | * | 2/1990 | Garren et al. ................ | 606/192 |
| 5,084,061 A | * | 1/1992 | Gau et al. .................... | 606/195 |
| 5,330,486 A | | 7/1994 | Wilk | |
| 5,746,762 A | * | 5/1998 | Bass ............................ | 606/192 |
| 6,254,570 B1 | * | 7/2001 | Rutner et al. ............ | 604/101.02 |
| 6,535,764 B2 | | 3/2003 | Imran et al. | |
| 6,675,809 B2 | | 1/2004 | Stack et al. | |
| 6,976,951 B2 | * | 12/2005 | Connors et al. ................ | 600/29 |
| 7,020,531 B1 | | 3/2006 | Colliou et al. | |
| 7,025,791 B2 | | 4/2006 | Levine et al. | |
| 7,037,344 B2 | | 5/2006 | Kagan et al. | |

(Continued)

FOREIGN PATENT DOCUMENTS

| | | |
|---|---|---|
| CA | 2534118 A1 | 3/2005 |
| EP | 01366716 | 12/2003 |

(Continued)

OTHER PUBLICATIONS

International Search Report dated Jul. 14, 2008 for PCT/US2008/02269.

*Primary Examiner* — Darwin Erezo
*Assistant Examiner* — Jonathan Hollm
(74) *Attorney, Agent, or Firm* — Barnes & Thornburg LLP

(57) ABSTRACT

The present invention provides an endoscopically implantable weight control device that forms a gastric outlet obstruction in a patient's digestive tract. The weight control device includes an inflatable body residing within the patient's pylorus and between the stomach and duodenum. The body features a first bulbous portion and a second bulbous portion, the exterior dimensions of the first bulbous portion exceeding the exterior dimension of the second bulbous portion. The body also includes an intermediate portion with exterior dimensions that are less than the exterior dimensions of both the first and second bulbous portions, wherein the intermediate portion resides within the patient's pyloric valve when the device is implanted. An internal passageway extends through the body, wherein the passageway receives and allows for the passage of chyme from the stomach to the duodenum. A method of treating obese patients with the inflatable weight control device utilizing a sequence of different-sized devices is also provided.

22 Claims, 6 Drawing Sheets

(56) References Cited

U.S. PATENT DOCUMENTS

| | | | |
|---|---|---|---|
| 2001/0008970 A1* | 7/2001 | Ravenscroft et al. | 606/198 |
| 2001/0016727 A1* | 8/2001 | Maki et al. | 604/509 |
| 2002/0049402 A1* | 4/2002 | Peacock et al. | 604/8 |
| 2002/0055757 A1* | 5/2002 | Torre et al. | 606/192 |
| 2002/0188354 A1 | 12/2002 | Peghini | |
| 2003/0216749 A1 | 11/2003 | Ishikawa et al. | |
| 2004/0039452 A1 | 2/2004 | Bessler | |
| 2004/0220682 A1 | 11/2004 | Levine et al. | |
| 2004/0249362 A1 | 12/2004 | Levine et al. | |
| 2005/0033331 A1 | 2/2005 | Burnett et al. | |
| 2005/0055039 A1 | 3/2005 | Burnett et al. | |
| 2005/0075622 A1 | 4/2005 | Levine et al. | |
| 2005/0080395 A1 | 4/2005 | Levine et al. | |
| 2005/0080431 A1 | 4/2005 | Levine et al. | |
| 2005/0080491 A1 | 4/2005 | Levine et al. | |
| 2005/0085923 A1 | 4/2005 | Levine et al. | |
| 2005/0125020 A1 | 6/2005 | Meade et al. | |
| 2005/0125075 A1 | 6/2005 | Meade et al. | |
| 2005/0228428 A1* | 10/2005 | Ali et al. | 606/194 |
| 2005/0228504 A1 | 10/2005 | Demarais | |
| 2005/0245788 A1 | 11/2005 | Gerber | |
| 2005/0273060 A1 | 12/2005 | Levy et al. | |
| 2005/0288552 A1* | 12/2005 | Barthel | 600/116 |
| 2006/0009858 A1 | 1/2006 | Levine et al. | |
| 2006/0020278 A1 | 1/2006 | Burnett et al. | |
| 2007/0135831 A1 | 1/2007 | Burnett | |
| 2007/0083224 A1* | 4/2007 | Hively | 606/192 |
| 2007/0178160 A1 | 8/2007 | Burnett | |
| 2007/0250132 A1 | 10/2007 | Burnett | |

FOREIGN PATENT DOCUMENTS

| | | |
|---|---|---|
| EP | 01569582 | 9/2005 |
| EP | 01610719 | 1/2006 |
| EP | 01610720 | 1/2006 |
| WO | WO2004/049982 | 6/2004 |
| WO | WO2004/087014 | 10/2004 |
| WO | WO2004/087233 | 10/2004 |
| WO | WO2005/060869 | 7/2005 |
| WO | WO2005/060882 | 7/2005 |
| WO | WO2005/082296 | 9/2005 |
| WO | WO2005/104989 | 11/2005 |
| WO | WO2006/016894 | 2/2006 |
| WO | WO2006/034062 | 3/2006 |

* cited by examiner

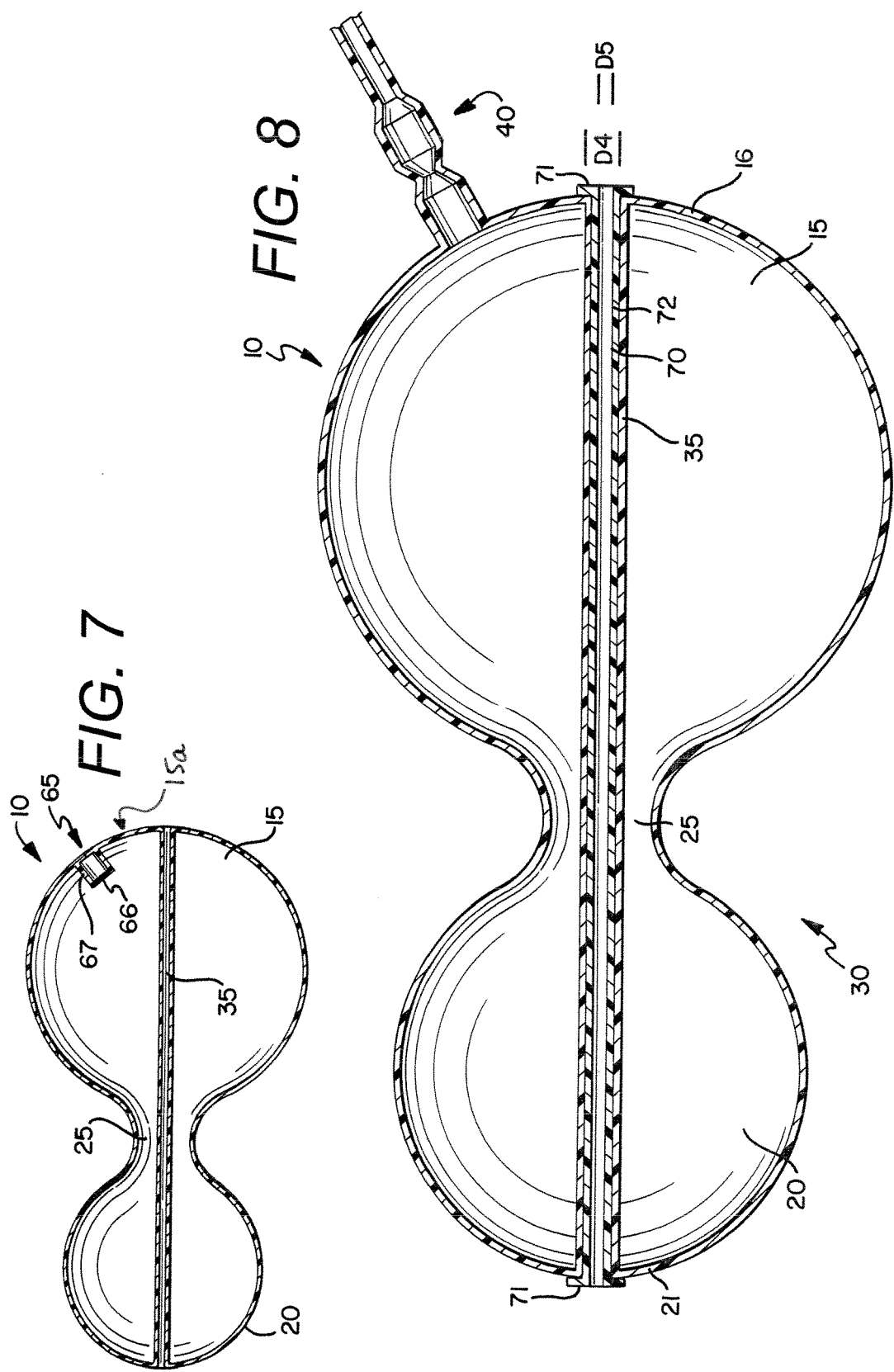

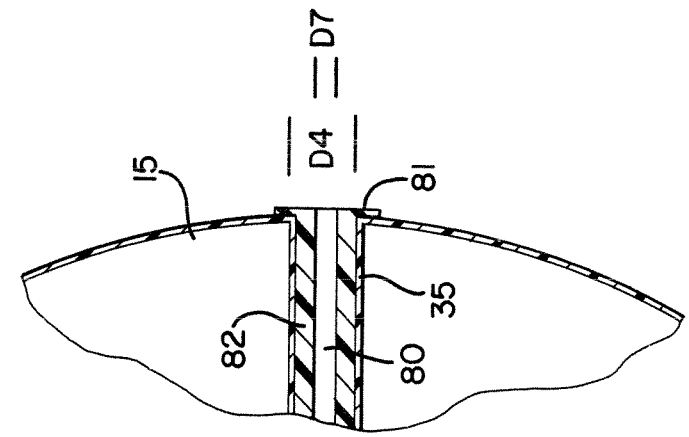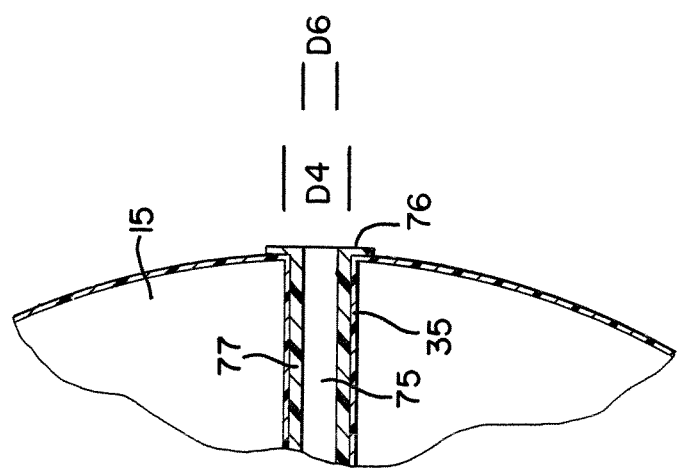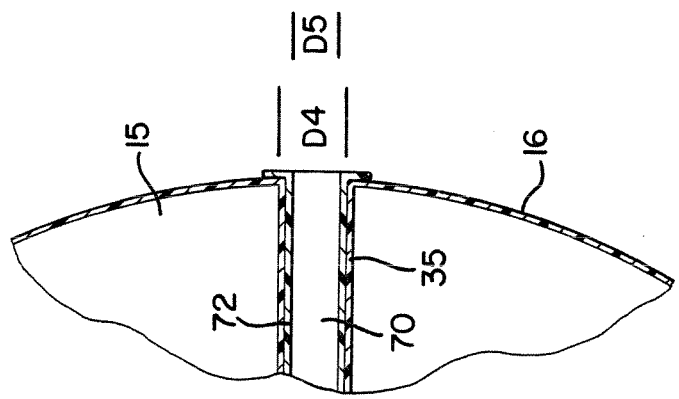

IMPLANTABLE WEIGHT CONTROL DEVICE

CROSS-REFERENCE TO RELATED APPLICATIONS

Not Applicable.

FEDERALLY SPONSORED RESEARCH OR DEVELOPMENT

Not Applicable.

TECHNICAL FIELD

The present invention provides an inflatable weight control device that is implanted with an endoscope. Once inflated, the device is retained within the patient's pyloric valve to form a gastric outlet obstruction wherein chyme can only pass through a central passageway in the device to reach the patient's duodenum.

BACKGROUND OF THE INVENTION

According to the Center for Disease Control (CDC), the prevalence of overweight and obesity has increased sharply for both adults and children over the past 30 years. Between 1976-1980 and 2003-2004, the prevalence of obesity among adults aged 20-74 years increased from 15.0% to 32.9%. Among young people, the prevalence of overweight increased from 5.0% to 13.9% for those aged 2-5 years, 6.5% to 18.8% for those aged 6-11 years, and 5.0% to 17.4% for those aged 12-19 years. Overweight and obesity ranges are determined by using weight and height to calculate a number called the "body mass index" (BMI). BMI is used because, for most people, it correlates with their amount of body fat. An adult who has a BMI between 25 and 29.9 is considered overweight, while an adult who has a BMI of 30 or higher is considered obese. Within the obesity category, a person is morbidly obese if he meets one of three criteria: a BMI over 35, at least 100 lbs. overweight, or 100% above ideal body weight; and a person is super-obese if he weighs in excess of 350 lbs.

It is well recognized that being overweight or obese raises many significant health implications. For example, obesity increases the risk of many diseases and health conditions, including: hypertension, dyslipidemia (for example, high total cholesterol or high levels of triglycerides), type 2 diabetes, coronary heart disease, stroke, gallbladder disease, osteoarthritis, sleep apnea, and respiratory problems. In addition to the health implications, overweight and obesity have a significant economic impact on the U.S. health care system. Medical costs associated with overweight and obesity may involve direct and indirect costs. Direct medical costs may include preventive, diagnostic, and treatment services related to obesity. Indirect costs relate to morbidity and mortality costs, where morbidity costs are defined as the value of income lost from decreased productivity, restricted activity, absenteeism, and bed days, and mortality costs are the value of future income lost by premature death. According to a study of national costs attributed to both overweight (BMI 25-29.9) and obesity (BMI greater than 30), medical expenses accounted for 9.1 percent of total U.S. medical expenditures in 1998 and may have reached as high as $78.5 billion ($92.6 billion in 2002 dollars). Approximately half of these costs were paid by Medicaid and Medicare. A more recent study focused on state-level estimates of the total obesity attributable direct medical expenditures. State-level estimates range from $87 million (Wyoming) to $7.7 billion (California). Obesity-attributable Medicare estimates range from $15 million (Wyoming) to $1.7 billion (California), and obesity-attributable Medicaid expenditures range from $23 million (Wyoming) to $3.5 billion (New York). The state differences in obesity-attributable expenditures are partly driven by the differences in the size of each state's population.

According to the CDC, overweight and obesity are a result of energy imbalance over a long period of time due to a combination of several factors. These factors include, individual behaviors, environmental factors, and genetics. Energy imbalance results when the number of calories consumed is not equal to the number of calories used. When the quantity of calories consumed is greater than calories used, weight gain results. In the United States and many other highly developed countries, the growing prevalence of pre-packaged foods, fast food restaurants, and soft drinks, that tend to be high in fat, sugar, and calories, increase a person's calorie consumption. In addition, portion size has also increased which causes people to eat more during a meal or snack, thereby increasing their calorie consumption. If the body does not burn off the extra calories consumed from larger portions, fast food, or soft drinks, weight gain will likely occur. Despite the well-known benefits of being physically active, most Americans lead a sedentary life style. According to the Behavioral Risk Factor Surveillance System, in 2000 more than 26% of adults reported limited or no physical activity during the course of an average week. Regarding the environmental factor, people may make decisions based on their environment or community. For example, a person may choose not to walk to the store or to work because of a lack of sidewalks. Genetics have been proven to play a role in obesity. For example, genes can directly cause obesity in disorders such as Bardet-Biedl syndrome and Prader-Willi syndrome. However, genes do not always predict future health; in some cases multiple genes may increase one's susceptibility for obesity and require outside factors, such as abundant food supply or little physical activity.

Conventional approaches to combat overweight and obesity have led doctors to surgically modify patients' anatomies in an attempt to reduce consumption by inducing satiety or a "full" feeling in the patient, thereby reducing the desire to eat. Examples include stomach stapling, or gastroplasties, to reduce the volumetric size of the stomach. In addition, two procedures, the Roux-en-Y gastric bypass and the biliopancreatic diversion with duodenal switch (BPD), reduce the size of the stomach and the effective-length of intestine available for nutrient absorption. These two procedures reduce the stomach volume and the ability of a patient to consume food. In an attempt to limit nutrient absorption in the digestive tract, at least one company has introduced a sleeve that is implanted in obese patients. U.S. Pat. No. 7,025,791 discloses a bariatric sleeve that is anchored in the stomach and extends through the pylorus and duodenum and beyond the ligament of Treitz. All chyme exiting the stomach is funneled through the sleeve and bypasses the duodenum and proximal jejunum. By directing the chyme through the sleeve, the digestion and absorption process in the duodenum is interrupted because the chyme cannot mix with the fluids in the duodenum. Because there is no mixing of bile with the chyme until the jejunum, the absorption of fats and carbohydrates is reduced. Although these conventional methods and approaches have had some success, they suffer from a number of limitations including high correction and mortality rates. Also, conventional methods are costly and prone to adaptation by the patient's digestive tract which reduces the effectiveness of the method.

Accordingly there is a need for an implantable weight loss device that is effective in prompting satiety while being minimally invasive and not irritable to patients over time. At the same time, there is a need to provide a weight control device that can be implanted with an endoscope during a visit to a doctor's office, and that does not require a hospital visit. Finally, it would be advantageous to provide treatment methods for combating overweight or obesity based upon the weight loss device that forms a gastric outlet obstruction in the stomach to prompt satiety and reduce food consumption.

SUMMARY OF THE INVENTION

The present invention provides a weight control device that is implanted and inflated with an endoscope in a patient's digestive track to form a gastric outlet obstruction. The weight control device resides within the pylorus and between the duodenum and stomach. The weight control device includes an internal passageway which forms a conduit for the reception and passage of chyme from the stomach through the pylorus and to the duodenum.

According to one aspect of the invention, the weight control device includes a first bulb, a second bulb, and an intermediate portion which collectively define an inflatable body. The internal passageway extends through the body, wherein the passageway receives and allows for the passage of chyme from the stomach to the duodenum. In a use position, the first bulb engages an inner surface of the pyloric antrum. This engagement prevents chyme from passing there between and as a result, chyme must pass through the internal passageway to exit the stomach. In the use position, the second bulb engages an inner surface of the pyloric canal, wherein the second bulb resides between the duodenum and the pyloric valve. Also in the use position, the intermediate portion of the body engages an inner surface of the pyloric valve.

According to another aspect of the invention, the collapsed body is inserted through the patient's mouth and through both the esophagus and stomach with the endoscope. A filling tube associated with the endoscope supplies saline through the valve and into the body until the device is sufficiently inflated to form the gastric outlet obstruction. To remove an implanted device, the body is deflated, such as by piercing the first bulb, and the endoscope is used to remove the deflated body.

According to another aspect of the invention, methods of treating overweight and/or obesity involve the inventive device. A first treatment method involves the staggered implantation of devices having different sized internal passageways to counter the digestive tract's accommodation of an implanted device. In a first treatment step, a first device having an internal passageway with a first diameter is implanted within the patient's pylorus. When the digestive tract adapts to the first device and weight loss stagnates, a second treatment step is employed. The second treatment step involves the replacement of the first device with a second device having an internal passageway that is smaller than that of the first device. While the second device continues to provide a gastric outlet obstruction in the stomach that blocks the normal passage of chyme from the stomach and that redirects chyme into the passageway, the passageway has reduced dimensions that reduce the volume of chyme that may pass through the device. When the digestive tract adapts to the second device and weight loss again stagnates, a third treatment step is commenced. The third treatment step consists of replacing the second device with a third device having an internal passageway that is smaller than both the first and second devices. Like the first and second devices, the third device provides a gastric outlet obstruction in the stomach that blocks the normal passage of chyme from the stomach and that redirects chyme into the passageway. Because less chyme is able to pass through the passageway of the third device compared to the passageway of both the first and second devices, an even greater amount of chyme accumulates proximate the first bulb and within the stomach leading the patient to feel full and stop consuming food.

A second treatment method involves the sequenced use of removable inserts placed within the passageway to counter the digest tract's accommodation of the device. In a first stage of the treatment method, the device is implanted within the patient's pylorus. When the patient's digestive tract begins to accommodate the device and weight loss stagnates, the second stage of the treatment method commences by placing a first insert into the passageway to reduce the diameter of the passageway. Depending upon whether the digestive track continues to adapt to the device, different sized inserts may be employed to reduce the volumetric capacity of the passageway. As a result, the amount of chyme that may pass through the device is reduced, which increases the accumulation of chyme within the stomach, leading the patient to feel full and stop consuming food.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 7 is a perspective view of a second embodiment of a weight control device, showing the device having an internal fill valve;

FIG. 8 is a cross-sectional view of the weight control device of FIG. 1, showing a removable insert positioned within the passageway of the device;

FIG. 9 is a partial cross-sectional view of a third embodiment of a weight control device, showing a first-sized removable insert positioned within the passageway of the device;

FIG. 10 is a partial cross-sectional view of the weight control device of FIG. 9, showing a second-sized removable insert positioned within the device passageway;

FIG. 11 is a partial cross-sectional view of the weight control device of FIG. 9, showing a third-sized removable insert positioned within the device passageway;

DETAILED DESCRIPTION

The present invention is not intended to be limited to the above-mentioned embodiment. It is easily understood for those ordinary skilled in the art that there are also various modifications or alternatives without departing the conception and principle of the present invention. The scope of the present invention is defined by the appended claims.

FIGS. 1-12 depict an inflatable weight control device 10 that is implanted in a patient's digestive track to form a gastric outlet obstruction 19. As explained in greater detail below, an endoscope is used to implant the weight control device 10 within the pylorus A and between the duodenum B and stomach C. While the human digestive track includes many components, only those that are relevant to the present invention are shown in the Figures. The pylorus A is the region of the stomach C that connects to the duodenum B, and that includes three parts: the pyloric antrum D which connects to the body of the stomach C; the pyloric canal E which connects to the duodenum B; and, the pyloric sphincter or valve F which is a ring of muscle that allows for the passage of chyme from the stomach C to the duodenum B. Once inflated, the configuration of the device 10 retains it within the pylorus A and prevents unintended movement into the duodenum B or stomach C. The stomach C consists of four coats or layers: the serous coat, the muscular coat, the areolar or submucous coat, and the mucous membrane, together with an assortment of vessels and nerves. The weight control device 10 includes an internal passageway which forms a conduit for the reception and passage of chyme from the stomach through the pyloric valve and to the duodenum. Chyme is the liquid substance produced in the stomach C before passing through the pyloric valve F and entering the duodenum B. Chyme is highly acidic (a pH value of approximately 2) and consists of partially digested food, water, hydrochloric acid, and various digestive enzymes. In the absence of the inventive device 10, chyme passes through the pyloric valve F and into the duodenum B, where the extraction of nutrients begins.

Figure 1:
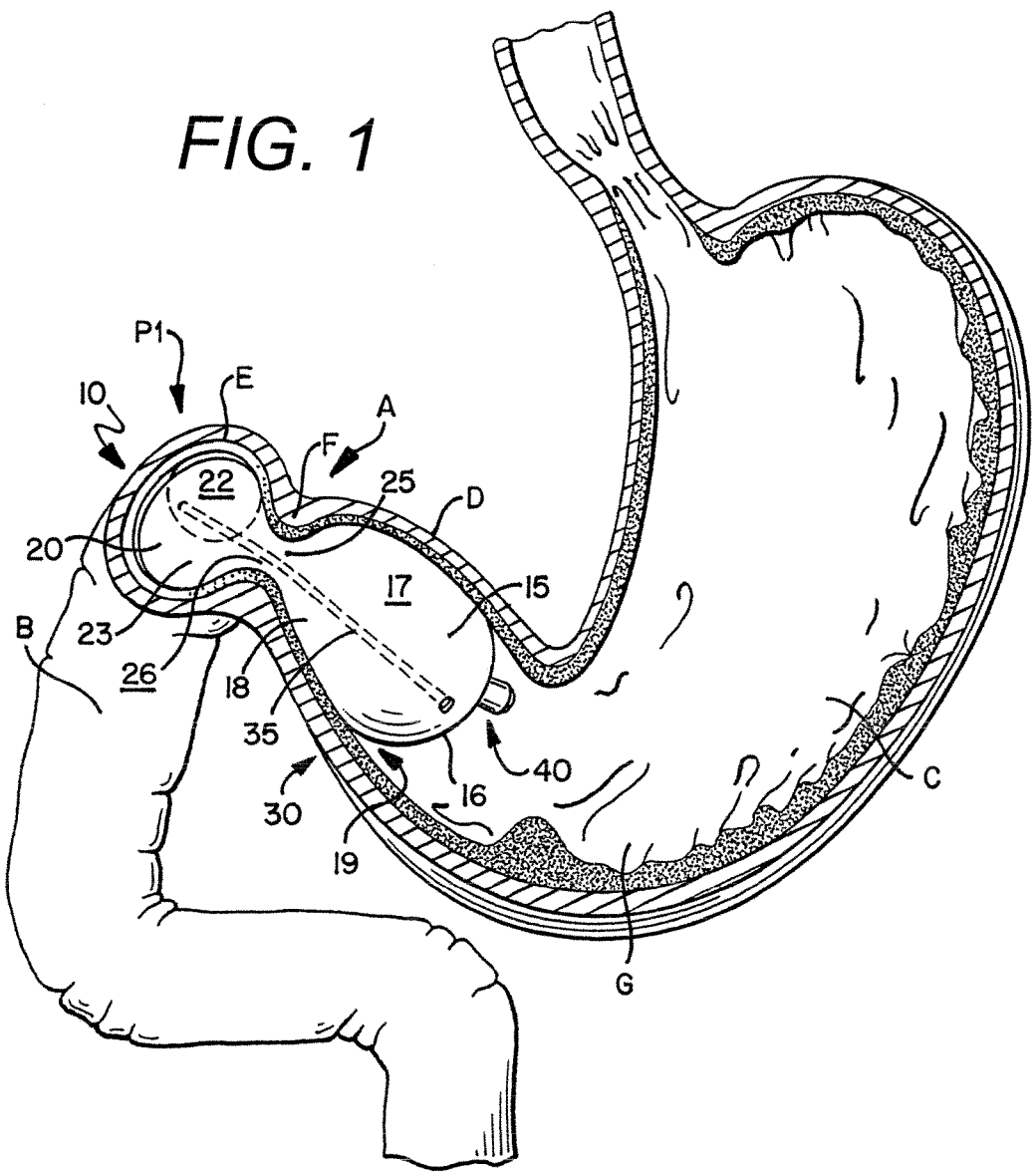
FIG. 1 is a perspective view of a first embodiment of a weight control device implanted within a patient's stomach.
Figure 3:
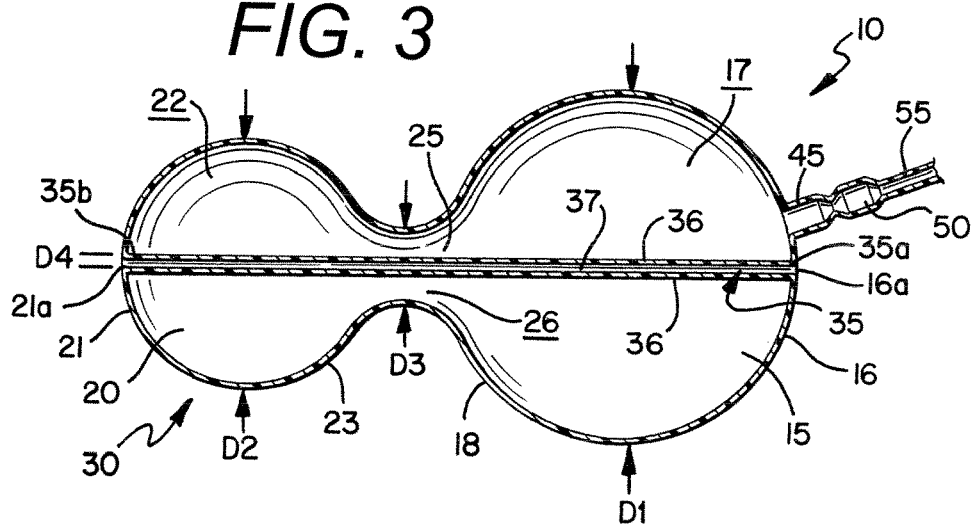
FIG. 3 is a cross-sectional view of the weight control device of FIG. 1, showing an internal passageway of the device.
Figure 12:
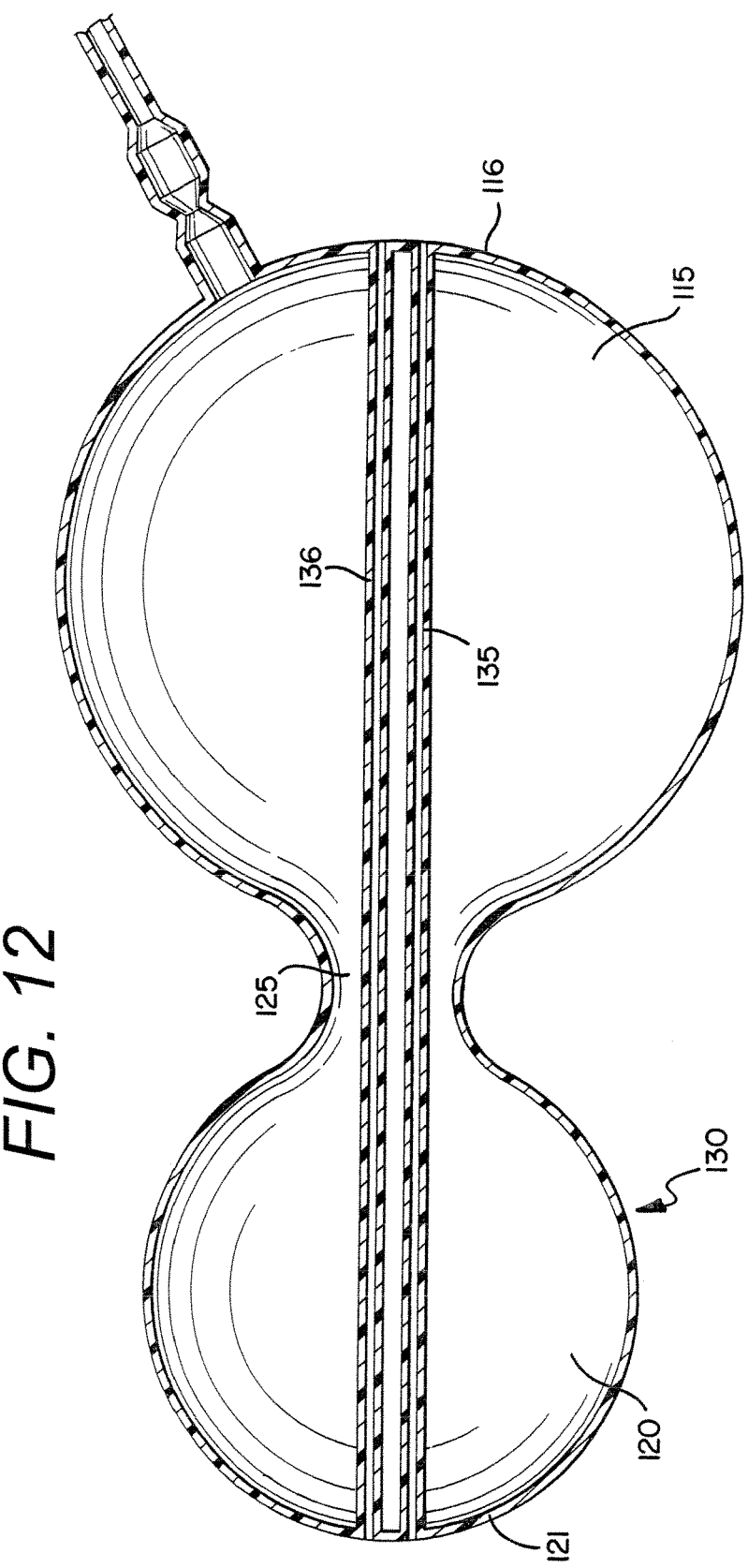
FIG. 12 is a cross-sectional view of a fourth embodiment of a weight control device, showing the device having two internal passageways.

The weight control device 10 includes a first bulbous portion or first bulb 15, a second bulbous portion or second bulb 20, and an intermediate portion 25. These components collectively define an inflatable body 30 with a "dumbbell" configuration. As shown in FIG. 1, the body 30 extends between the pyloric antrum D and the pyloric canal E, and through the pyloric valve F. Unlike conventional weight control devices, such as the elongated sleeve of U.S. Pat. No. 7,025,791 that extends through the duodenum B, the second bulb 20 resides within the pyloric canal E and does not extend into the duodenum B. Also unlike the sleeve of the '791 patent, the body 30 has opposed cavities or bulbs 15, 20 that extend from a common segment, the intermediate portion 25, and that is inflatable with the endoscope H. In one embodiment, the intermediate portion 25 is semi-rigid compared to the more flexible first and second bulbs 15, 20, wherein the contractions of pyloric valve F do not collapse the intermediate portion. To increase the rigidity of the intermediate portion 25, the wall thickness of the intermediate portion 25 is greater than that of the first and second bulbs 15, 20. Also, the intermediate portion 25 may be formed from a material with greater strength and/or rigidity properties than that used to form the first and second bulbs 15, 20. Unlike the sleeve of the '791 patent, which holds the pyloric valve F open to induce a "dumping syndrome," the intermediate portion 25 is engaged and contracted to a small extent by the pyloric valve F. The device 10 includes at least one internal passageway or lumen 35 extending through the body 30, wherein the passageway 35 receives and allows for the passage of chyme from the stomach C to the duodenum B. Referring to FIG. 3, the internal passageway 35 extends from an end wall 16 of the first bulb 15 through the intermediate portion 25 and to an end wall 21 of the second bulb 20. Further, the passageway 35 includes a first end 35a aligned with an opening 16a in the end wall 16, and a second end 35b aligned with an opening 21a in the end wall 21. In a preferred embodiment of the weight control device 10, the passageway 35 represents the longitudinal axis of the body 30. The internal passageway 35 is defined by two substantially parallel walls 36 that are spaced a distance apart to define a cavity 37. In the embodiment of FIG. 12, the body 130 includes a first internal passageway 135 and a second internal passageway 136 extending between the end wall 116 of the first bulb 115 and the end wall 121 of the second bulb 120, and through the intermediate portion 125. Thus, the first and second passageways 135, 136 provide the body 130 with two conduits for the passage of chyme from the stomach C to the duodenum B. In a slight variation of the body 130, the first and second internal passageways 135, 136 may converge, such as aft of the intermediate portion 125, to define a common exit passageway in the second bulb 120.

When the weight control device 10 is implanted and inflated to define an installed or use position P1 (see FIG. 1), an exterior surface 17 of the first bulb 15 engages an inner surface of the pyloric antrum D. Thus, the first bulb 15 resides between the stomach corpus G (the central body portion of the stomach) and the pyloric valve F. In the use position P1, the first bulb 15 effectively seals the pyloric antrum D to prevent the normal flow of chyme from the stomach B into the pyloric valve F and forces or directs chyme into the internal passageway 35. Because the body 30 is inflatable, the dimensions of the first bulb 15 can be customized during inflation to match the dimensions of the pyloric antrum D to facilitate sealing engagement between the bulb surface 17 and the inner surface of the pyloric antrum D. This sealing engagement results in a gastric outlet obstruction 19 (see FIG. 1) that causes chyme to accumulate proximate the first bulb 15 prior to entering the internal passageway 35. The obstruction also prevents chyme from departing the pyloric antrum D and as a result, chyme must pass through the internal passageway 35 to exit the stomach. As a result of the engagement, the first bulb 15 provides a gastric outlet obstruction 19 in the stomach C that (i) prevents the normal passage of chyme from the stomach C through the pylorus; (ii) redirects chyme into the passageway 35; and, (iii) reduces the volumetric capacity of the stomach C thereby causing the patient to feel satiated or "full" after consuming a reduced amount of food. Lastly, the engagement between the first bulb 15 and the pyloric antrum D retains the body 30 in the use position P1 such that the properly inflated first bulb 15 cannot pass beyond the pyloric valve F and into the duodenum B. As shown in FIG. 1, the first bulb 15 has exterior dimensions that exceed the dimensions of the pyloric valve F whereby the first bulb 15 is prevented from passing beyond the valve F and into the duodenum B. In a preferred embodiment of the device 10, a first interface region or shoulder 18 (see FIGS. 1-3) is defined between the first bulb 15 and the intermediate portion 25. The interface region 18 has a tapered, annular configuration and engages the pyloric antrum D adjacent to the pyloric valve F. In the use position P1, the first bulb 15 has a diameter D1 that is 4-9 centimeters (cm), and preferably the diameter D1 is 5-8 cm.

In the use position P1, an exterior surface 22 of the second bulb 20 engages an inner surface of the pyloric canal E, wherein the second bulb 20 resides between the duodenum B and the pyloric valve F. The engagement between the second bulb 20 and the pyloric canal E retains the body 30 in the use position P1 such that the properly inflated second bulb 20 cannot pass through the pyloric valve F and into the pyloric antrum D or stomach corpus G. Referring to FIG. 1, the opening 21a in the end wall 21 of the second bulb 20 is oriented such that chyme discharged from the passageway 35 is directed into the duodenum B. In a preferred embodiment of the device 10, a second interface region or shoulder 23 (see FIGS. 1-3) is defined between the second bulb 20 and the intermediate portion 25. The interface region 23 has a tapered, annular configuration and engages the pyloric canal E adjacent to the pyloric valve F. Once inflated and implanted within a patient, the second bulb 20 has a diameter D2 that is 2-5 cm and preferably the diameter D2 is 3-4 cm. Also in the use position P1, an exterior surface 26 of the intermediate portion 25 engages an inner surface of the pyloric valve F, wherein the first bulb 15 engages the pyloric antrum B and the second bulb 20 engages the pyloric canal E. Described in a different manner, the pyloric valve F contracts about the intermediate portion 25. In the embodiment where the intermediate portion 25 is semi-rigid, the contraction of the pyloric valve F does not cause the intermediate portion 25 or the internal passageway 35 to completely collapse. In the use position P1, the intermediate portion 25 has a diameter D3 that is 1.0-2.5 centimeters, and preferably the diameter D3 is 1.5-2.0 cm. Due to the configuration of the body 30, the intermediate diameter D3 is less than both the first bulb diameter D1 and the second bulb diameter D2. The internal passageway 35 has a diameter D4 that is 1-6 millimeters (mm), and preferably the diameter D4 is 2-4 mm.

Figure 2:
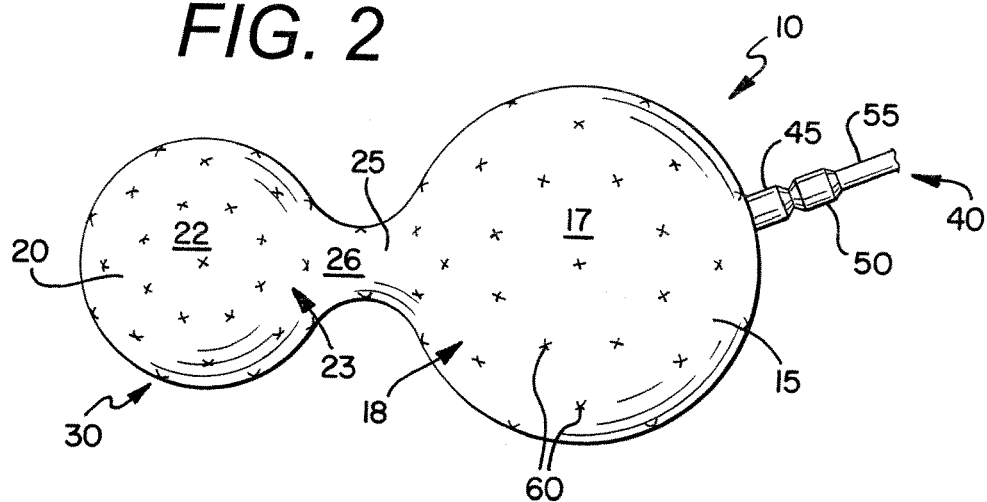
FIG. 2 is a perspective view of the weight control device of FIG. 1.
Figure 4:
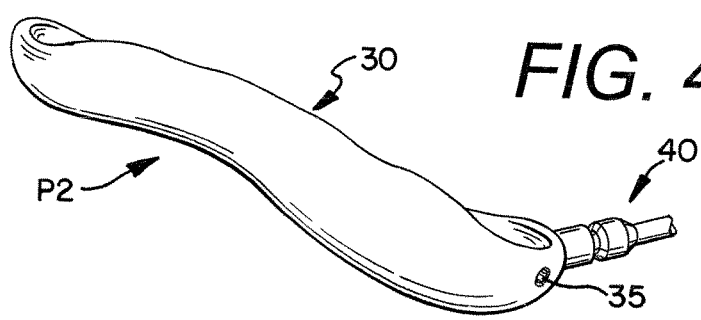
FIG. 4 is a perspective view of the weight control device of FIG. 1, showing the device in a pre-installed state wherein the device is deflated.

FIG. 4 depicts the device 10 in a collapsed or uninflated position P2, wherein the device 10 is flexible and ready to be implanted in a patient With the use of an endoscope H. A valve assembly 40 that is used to fill the device 10 with an inflation fluid, such as saline, extends from the first bulb 15. The valve assembly 40 includes a stem 45 that is grasped by the endoscope H see FIGS. 5 and 6) during the implantation process, a valve body 50, and fill tube segment 55 that can be severed after the device reaches the installed position P1. The valve body 50 has an internal, one-way valve that accepts the inflation fluid supplied by the endoscope H. Over time, the body 30 may require additional inflation fluid due to seepage or leakage. Alternatively, the valve body 50 has a two-way valve that allows for both the filling and removal of inflation fluid from the body 30. Preferably, the valve assembly 40 extends at off-center location from the first bulb 15 because the internal passageway 35 occupies the central axis of the body 30. In the event that the passageway 35 is not centrally located in the body 30, the valve assembly 40 should be offset from the passageway 35. In another embodiment, the body 30 includes an internal valve assembly 65 (see FIG. 7) that extends inward from an outer surface 15a of the first bulb 15. Like the valve assembly 40 of FIGS. 1-6, the assembly 65 includes a valve body 66 and an internal stem 67. Referring to FIG. 7, the valve assembly 65 lacks an external component, wherein there is a smooth interface between the valve assembly 65 and the outermost surface of the body 30. As a result of the smooth interface, the outer surface 15a of the first bulb 15 lacks external structure at the junction of the first bulb 15 and the stem 67 of the valve assembly 65. As shown in FIG. 2, the body 30 includes a plurality of radio opaque markers 60 that facilitate detection of the device 10 during testing subsequent to implantation. To counter the acids in the stomach A and to ensure a sufficient life of the body 30, the device 10 can be fabricated from one or more of the following materials: fluoropolymer, such as PTFE (polytetrafluoroethylene), PFA (perfluoroalkoxy polymer resin), FEP (fluorinated ethylene-propylene) or polyethylene, such as HDPE (high density polyethylene), MDPE (medium density polyethylene) or LDPE (low density polyethylene).

Figure 5:
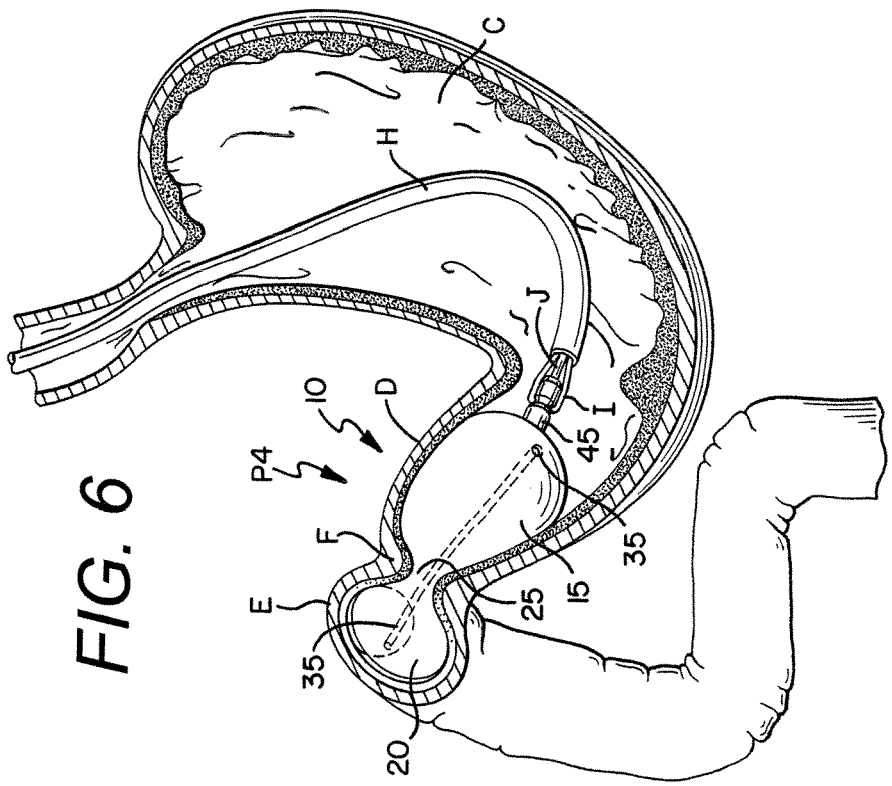
FIG. 5 is a perspective view of the weight control device of FIG. 1, showing the device during one step of the implantation process.
Figure 6:
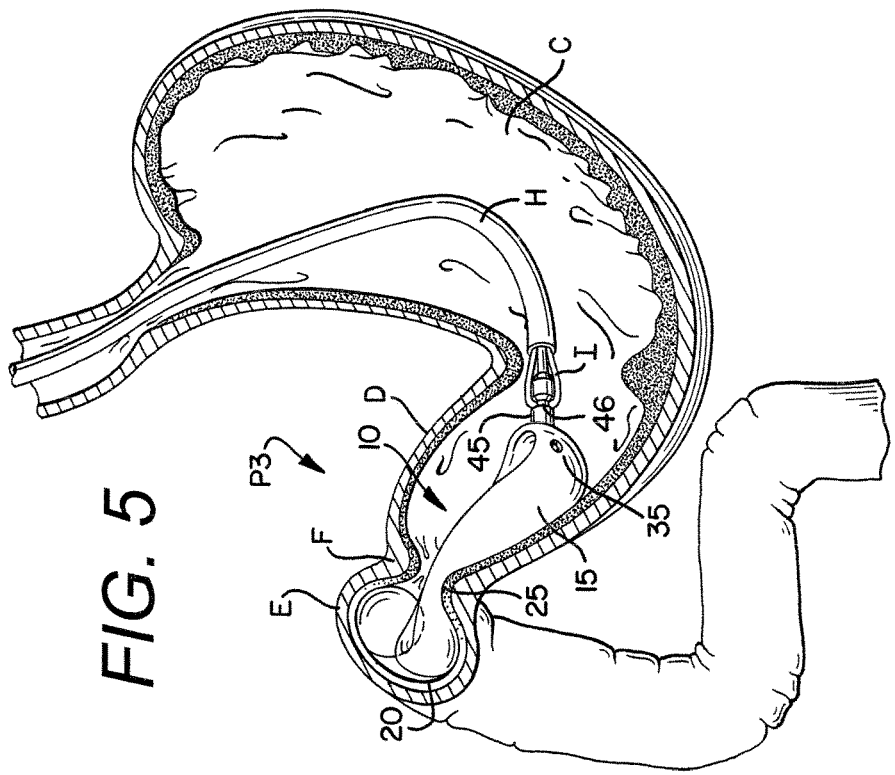
FIG. 6 is a perspective view of the weight control device of FIG. 1, showing the device during a second step of the implantation process.

FIG. 5 depicts an intermediate position P3 where the collapsed device 10 has been inserted through the stomach C and into the pylorus A by the endoscope H. The collapsed device 10 is inserted through the patient's mouth and through both the esophagus and stomach with the endoscope H. The endoscope H has a clamp I that grasps a groove 46 of the stem 45 to facilitate insertion of the device 10. In the intermediate position P3, the first bulb 15 resides within the pyloric antrum D, the second bulb 20 resides within the pyloric canal, and the intermediate portion 25 resides within the pyloric valve F. A filling tube J within the endoscope H supplies an inflation fluid, such as saline, through the valve 50 and into the body 30 until an inflated position P4 (see FIG. 6) is reached. Since the body 30 is an enclosed vessel, the inflation fluid fills the first bulb 15, the second bulb 20 and the intermediate portion 25 to inflate the body 30. In the inflated position P4, the endoscope H is coupled to the inflated body 30, wherein the exterior surface 17 of the first bulb 15 engages an inner surface of the pyloric antrum D, the exterior surface 22 of the second bulb 20 engages an inner surface of the pyloric canal E, and the exterior surface 26 of the intermediate portion 25 engages an inner surface of the pyloric valve F. Thus, in the inflated position P4, the device 10 is inflated such that the first bulb 15 engages the pyloric antrum B and the second bulb 20 engages the pyloric canal E, both adjacent the pyloric valve F. After the inflated position P4 is reached, the endoscope H is de-coupled from the valve assembly 40 and removed from the patient whereby the device 10 is ready for use. To remove an implanted device 10, the body 30 is deflated, such as by piercing the first bulb 15, and the endoscope H is used to remove the deflated body 30.

After the device 10 has been implanted and is in the use position P1, the device 10 provides a method of treating obese patients. The method comprises the sequenced implantation of devices 10 having different sized passageways 35 to counter the digestive tract's accommodation of an implanted device 10. In a first treatment step, a first device 10 having the internal passageway 35 with a diameter D4, such as 4.0 millimeters, is implanted within the patient's pylorus A at the use position P1. Thus, the first bulb 15 provides a gastric outlet obstruction 19 in the stomach C that blocks the normal passage of chyme from the stomach C and that redirects chyme into the passageway 35. The resulting gastric outlet obstruction 19 reduces the volumetric capacity of the stomach C thereby causing the patient to feel "full" resulting in appetite suppression, after consuming a reduced quantity of food. Initially, the patient will feel full and stop consuming food or reduce the rate of food consumption, which will lead to an initial phase of weight loss during the first treatment step. However, over time, the patient's digestive tract will adapt to the first device 10, the patient will not feel full after consuming a similar quantity of food, and the weight loss experienced during the initial phase will stagnate.

A second treatment step is designed to combat the stagnation in weight loss experienced during the first step by using a different-sized second device 10 in place of the first device 10. Specifically, the first device 10 is removed from the patient and replaced by the second device 10 which has an internal passageway 35 with a reduced diameter D4, such as 3.0 mm. Thus, the passageway diameter D4 of the second device 10 is less than that of the first device 10 and the volume of the passageway 35 is reduced as well. While the second device 10 continues to provide a gastric outlet obstruction 19 in the stomach C that blocks the normal passage of chyme from the stomach C and that redirects chyme into the passageway 35, the passageway 35 has reduced dimensions that reduce the volume of chyme that may pass through the device 10. Because less chyme is able to pass through the passageway of the second device 10 compared to the passageway of the first device 10, a greater amount of chyme accumulates within the stomach C leading the patient to feel full and stop consuming food. This will lead to weight loss during the early phase of the second treatment step, however, the patient's digestive tract will adapt to the second device 10 over time. Accordingly, the patient will not feel full after consuming a similar quantity of food, and the weight loss experienced during the early phase will again stagnate.

To combat the stagnation in weight loss experienced during the second step, a third treatment step involves replacing the second device 10 with a different-sized third device 10. Specifically, the second device 10 is replaced by the third device 10 which has an internal passageway 35 with a further reduced diameter D4, such as 2.0 mm. Thus, the passageway diameter D4 of the third device 10 is less than that of both the first and second devices 10. Like the first and second devices 10, the third device 10 provides a gastric outlet obstruction 19 in the stomach C that blocks the normal passage of chyme from the stomach C and that redirects chyme into the passageway 35. Due to the reduced diameter D4, the passageway 35 accepts an even smaller volume of chyme for transmission through the pylorus A and to the duodenum B. Because less chyme is able to pass through the passageway 35 of the third device 10 compared to the passageway 35 of both the first and second devices 10, an even greater amount of chyme accumulates proximate the first bulb 15 and within the stomach C leading the patient to feel full and stop consuming food.

Assuming the same quantity of food is consumed in the same time interval with each of the three different sized devices 10, a greater amount of chyme is transmitted through the passageway 35 of the first device 10 compared to either of the second or third devices 10. Also, a greater amount of chyme is transmitted through the passageway 35 of the second device 10 compared to the third device 10. Under these same conditions, the quantity of chyme obstructed by the bulb 15 and accumulating within the stomach corpus G is greater for the third device 10 compared to the second device 10, and greater for the second device 10 compared to the first device 10. Therefore, the present invention provides a method of treating obesity with the implantation of devices 10 having different sized internal passageways 35 which reduce the volume of chyme passing through the body 30, increase the accumulation of chyme within the stomach C, and hasten the patient to feel full and reduce or halt food consumption. Because this method of treatment counters the digestive tract's natural tendency to accommodate a single device 10, the patient should continue to experience weight loss.

A second obesity treatment method is shown in FIGS. 8-11 and involves the use of removable inserts 70 of variable dimensions in the passageway 35 to counter the digest tract's accommodation of the device 10. In a first stage of the treatment method, the device 10 is implanted within the patient's pylorus A. Consistent with that explained above, the first bulb 15 provides a gastric outlet obstruction 19 in the stomach C that blocks the normal passage of chyme from the stomach C and that redirects chyme into the passageway 35 for transmission to the duodenum B. When the patient's digestive tract begins to accommodate the device 10 and weight loss stagnates, the second stage of the treatment method commences. Instead of replacing the existing device 10 with a device 10 having a smaller passageway 10, the second stage involves the insertion of a first insert 70, with the endoscope H, into the passageway 35 of the existing, implanted device 10 (see FIGS. 8 and 9). Since the device 10 is already inflated, the passageway 35 slidingly receives the first insert 70. The first insert 70 includes opposed end flanges 71 which engage the outer surfaces 16, 21 of the first and second bulbs 15, 20, respectively, to further secure the position of the insert 70 within the passageway 35. As mentioned above, the passageway 35 has a diameter D4 and the first insert 70 has a diameter D5 that is less than the passageway diameter D4. For example, the passageway diameter D4 is 5 mm and the first insert diameter D5 is 4 mm. The insert 70 has a wall arrangement 72 with a thickness that provides the insert diameter D5. Due to its reduced dimensions, the first insert 70 effectively reduces the volume of the passageway 35 which restricts the amount of chyme that may pass through the device 10 and which increases the accumulation of chyme within the stomach C, leading the patient to feel full and stop consuming food.

A second treatment stage is designed to combat the stagnation in weight loss experienced during the first stage by removing the first insert 70 and inserting a second insert 75 into the passageway 35 with an endoscope H. As shown in FIG. 10, the second insert 75 has a diameter D6 that is less than both the passageway diameter D4 and the first insert diameter D5. For example, the passageway diameter D4 is 5 mm, the first insert diameter D5 is 4 mm, and the second insert diameter D6 is 3 mm. The second insert 75 has an end flange 76 and a wall arrangement 77 with a thickness that provides the insert diameter D6. Like the first insert 70, the second insert 75 effectively reduces the volume of the passageway 35 which thereby restricts the amount of chyme that may pass through the device 10 and into the duodenum B. This restriction increases the accumulation of chyme within the stomach C, leading the patient to feel full and stop consuming food. To offset the stagnation in weight loss that may result in the second stage, a third treatment stage involves using the endoscope H to replace the second insert 75 with a third insert 80 in the passageway 35. Referring to FIG. 11, the third insert 80 has a diameter D7 that is less than the passageway diameter D4 and both the first and second insert diameters D5, D6. As an example, the passageway diameter D4 is 5 mm, the first insert diameter D5 is 4 mm, the second insert diameter D6 is 3 mm, and the third insert diameter D7 is 2 mm. The third insert 80 has an end flange 81 and a wall arrangement 82 with a thickness that provides the insert diameter D7. Like the first and second inserts 70, 75, the third insert 80 effectively reduces the volume of the passageway 35 which thereby restricts the amount of chyme that may pass through the device 10 and into the duodenum B for appetite suppression purposes.

Each of these methods provide sequenced protocols for treating obesity with the device 10. Because the device 10 is easy to implant, either treatment method may be utilized during an office visit without requiring a costly and time-consuming hospital visit for the patient. Once sufficiently inflated, the resulting obstruction causes chyme to accumulate proximate the first bulb 15 or to entering the internal passageway 35 where it is then transported through the inflatable body 35 and discharged from the second bulb 20 into the patient's duodenum B. The accumulation of chyme in the pyloric antrum D and the stomach A causes the patient to feel full and stop eating. Thus, these treatment methods provide a gastric outlet obstruction 19 that slows the passage of chyme into the duodenum B and as a result, the patient feels full and stops eating after consuming relatively small portions. Due to the sequenced nature of the first and second treatment methods, the gastric outlet obstruction 19 counteracts the stomach's attempt to accommodate the device 10 over time.

Numerous modifications may be made to the foregoing invention without departing from the basic teachings thereof. Although the present invention has been described in substantial detail with reference to one or more specific embodiments, those of skill in the art will recognize that changes may be made thereto without departing from the scope and spirit of the invention.

What is claimed is:

1. An endoscopically implantable weight control device that forms a gastric outlet obstruction in a patient's digestive tract, the weight control device comprising:
    an inflatable body adapted to reside within the patient's pyloric valve and between the patient's stomach and duodenum, the inflatable body consisting of:
        a first bulbous portion configured to reside within the patient's stomach, wherein the first bulbous portion is configured to engage the inner surface of the patient's pyloric antrum;
        an internal valve assembly extending inward from an opening formed in the outermost surface of the inflatable body, the valve assembly consisting essentially of an internal stem and an internal valve that delivers an inflation fluid to the first bulbous portion, wherein the internal stem extends inward from the outermost surface of the body to the internal valve residing below the outer body surface, wherein the valve assembly lacks an external component, and wherein the arrangement of the valve assembly provides a smooth interface between the valve assembly and the outermost surface of the body;
        a second bulbous portion configured to reside within the patient's duodenum, exterior dimensions of the first bulbous portion exceeding exterior dimensions of the second bulbous portion;
        an intermediate portion between the first and second bulbous portions, the intermediate portion having exterior dimensions less than the exterior dimensions of both the first and second bulbous portions, wherein the intermediate portion is configured to reside within and seal against the patient's pyloric valve when the device is implanted, wherein all of the first bulbous portion, the second bulbous portion and the intermediate portion are formed from one material, and wherein the entire intermediate portion has a rigidity that is greater than a rigidity of both the first and second bulbous portions; and,
        an internal passageway extending through the inflatable body, wherein the passageway receives and allows for the passage of chyme from the stomach to the duodenum.

2. The implantable weight control device of claim 1, wherein an exterior surface of the first bulbous portion is adapted to engage the inner surface of the pyloric antrum.

3. The implantable weight control device of claim 1, wherein an exterior surface of the intermediate portion is adapted to engage an inner surface of the pyloric valve.

4. The implantable weight control device of claim 1, wherein an exterior surface of the second bulbous portion is adapted to engage an inner surface of the pyloric canal.

5. The implantable weight control device of claim 1, wherein the internal passageway is centrally positioned along a longitudinal axis of the inflatable body and the internal valve assembly is positioned a substantial distance from the internal passageway in an off-center location of the first bulbous portion.

6. The implantable weight control device of claim 5, wherein the internal valve is a check valve.

7. The implantable weight control device of claim 1, wherein the internal passageway extends from an end wall of the first bulbous portion through the intermediate portion and to an end wall of the second bulbous portion.

8. The implantable weight control device of claim 1, wherein the internal passageway extends between an end wall of the first bulbous portion and an end wall of the second bulbous portion without extending beyond said end walls.

9. A weight control device that is implantable with an endoscope and that is configured to form a gastric outlet obstruction in a patient's digestive tract, the weight control device consisting essentially of:
    an inflatable body having a first inflatable bulb configured to engage the inner surface of the patient's pyloric antrum, a second inflatable bulb with a circumference less than a circumference of the first bulb, and an intermediate portion that is between the first and second bulbs and is adapted to reside within and seal the patient's pyloric valve between the stomach and duodenum when the device is implanted, wherein each of the first bulb and second bulb are integral with the intermediate portion to provide the inflatable body with a seamless, uninterrupted configuration, wherein all of the first bulb, the second bulb and the intermediate portion are formed from one material, and wherein the entire intermediate portion has a rigidity that is greater than a rigidity of both the first and second bulbs;
    an internal valve assembly extending inward from an opening formed in the outermost surface of the inflatable body, wherein the internal valve assembly consists of an internal stem that extends inward from the opening in the outermost body surface to an internal valve body that delivers an inflation fluid to the first bulb, wherein the valve assembly and the inflatable body lack an external component that obstructs the internal stem of the internal valve assembly;
    the inflatable body further having at least one internal passageway extending through the first and second bulbs without extending beyond an end wall of the first and second bulbs; and,
    wherein the at least one internal passageway is configured to pass chyme from the patient's stomach to the patient's duodenum.

10. The weight control device of claim 9, wherein the first bulb defines an obstruction that substantially prevents chyme, other than that passing through the at least one internal passageway, from reaching the pyloric valve and the duodenum.

11. The weight control device of claim 9, wherein first bulb is configured to engage an inner surface of the patient's stomach proximate the pyloric valve to prevent the first bulb from moving past the pyloric valve and into the duodenum.

12. The weight control device of claim 11, wherein the intermediate portion is configured to engage an inner surface of the patient's pyloric valve.

13. The weight control device of claim 11, wherein the second bulb is configured to engage an inner surface of the patient's pyloric canal proximate the pyloric valve.

14. The weight control device of claim 9, wherein the inflatable body has a dumbbell configuration, wherein a transition from the first bulb to the intermediate portion defines a first annular shoulder that is adapted to engage the terminal portion of the patient's stomach prior to the patient's pyloric valve.

15. The weight control device of claim 9, wherein the at least one internal passageway is centrally positioned along a longitudinal axis of the inflatable body and the valve assembly is positioned a substantial distance from the at least one internal passageway in an off-center location of the first bulb.

16. The weight control device of claim 9, wherein the at least one internal passageway extends from an end wall of the first bulb through the intermediate portion and to an end wall of the second bulb.

17. The weight control device of claim 9, further comprising a first insert that is removably inserted within the at least one internal passageway, the first insert having a diameter that is less than a diameter of the at least one internal passageway.

18. The weight control device of claim 17, further comprising a second insert that is removably inserted within the at least one internal passageway, the second insert having a diameter that is less than the diameter of both the first insert and the at least one internal passageway.

19. An endoscopically implantable weight control device configured to form a gastric outlet obstruction in a patient's digestive tract, the weight control device consisting essentially of:
    an inflatable body having a first inflatable bulb configured to engage the inner surface of the patient's pyloric antrum, a second inflatable bulb, and an intermediate portion that is between the first and second bulbs and is adapted to reside within and seal the patient's pyloric valve between the stomach and duodenum, wherein all of the first and second bulbs and the intermediate portion are integral and formed from one material;
    the inflatable body further having at least one internal central passageway extending between an end wall of the first bulb through the intermediate portion and to an end wall of the second bulb, wherein the at least one internal central passageway does not extend beyond either said end wall, and wherein the at least one internal central passageway receives and allows for the passage of chyme from the stomach to the duodenum; and,
    an internal valve assembly consisting of a stem and an internal valve, the stem extending inward from an off-center opening formed in an outermost surface of the inflatable body, wherein the valve assembly lacks an external component, and wherein the arrangement of the valve assembly provides a smooth interface between the valve assembly and the outermost surface of the body.

20. The weight control device of claim 19, wherein the weight control device is implanted with an endoscope in the patient's digestive tract in a deflated state, and then inflated such that the first bulb is adapted to engage an inner surface of the stomach proximate the pyloric valve and the intermediate portion engages an inner surface of the pyloric channel.

21. The weight control device of claim 19, further comprising:
    a first insert that is removably inserted within the at least one internal central passageway, the first insert having a diameter that is less than a diameter of the at least one internal central passageway; and,
    a second insert that is removably inserted within the at least one internal central passageway, the second insert having a diameter that is less than the diameter of both the first insert and the at least one internal central passageway.

22. The weight control device of claim 19, wherein the inflatable body has a pair of internal passageways extending from the end wall of the first bulb through the intermediate portion and to the end wall of the second bulb, wherein the passageways receive chyme from the stomach to the duodenum.

* * * * *